MINIATURE ROSE PLANT
Filed July 24, 1975
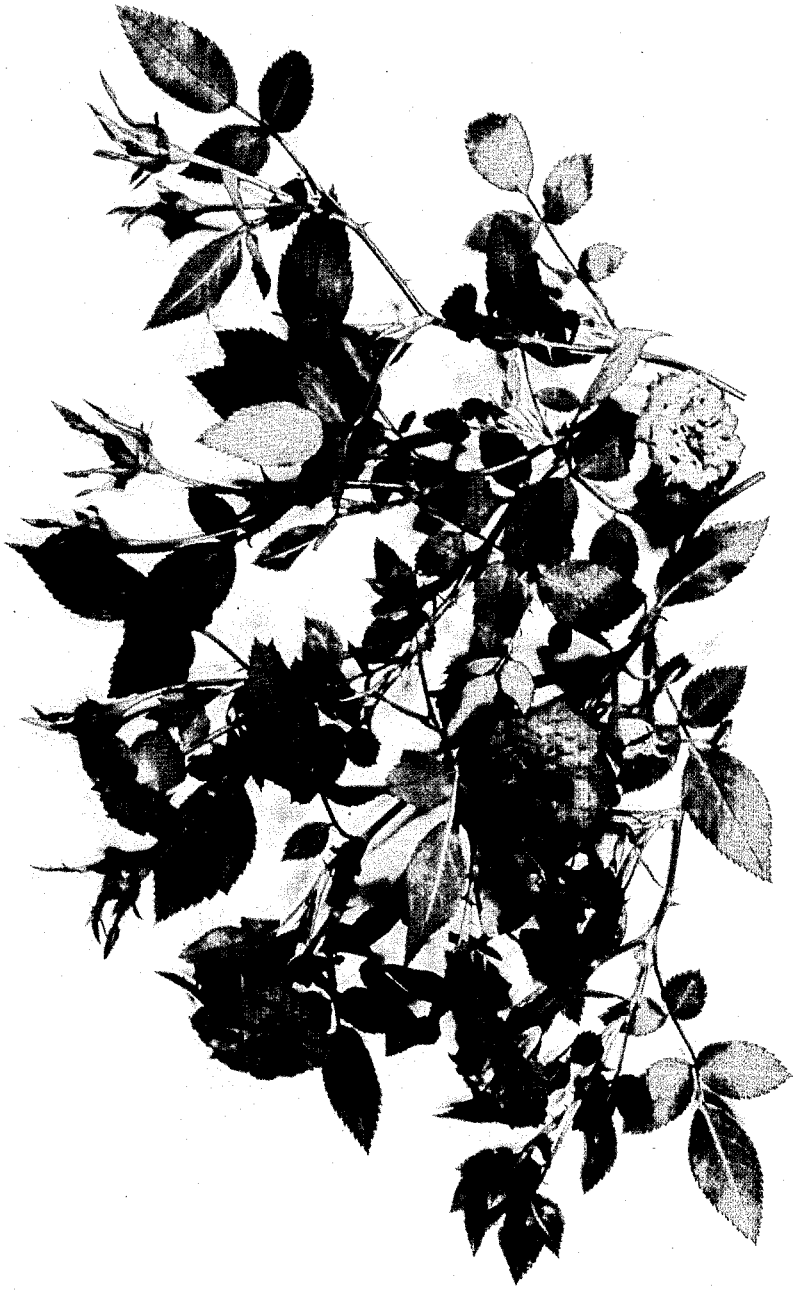

United States Patent

Plant Pat. 3,935
Patented July 6, 1976

3,935

MINIATURE ROSE PLANT

Ralph S. Moore, 2519 E. Noble Ave., Visalia, Calif. 93277

Filed July 24, 1975, Ser. No. 598,671
Int. Cl.[2] A01H *5/00*
U.S. Cl. Plt.—10 1 Claim

The present invention relates to a new and distinct variety of hardy, dwarf, bush type rose plant of the miniature class; the variety being primarily characterized—as to novelty—by deep red buds and flowers which in general color effect are rich dark red when grown outdoors (slightly lighter grown indoors in plastic greenhouse).

The variety is further characterized by:

An abundance of bloom, with flowers usually borne several to the stem in moderately tight clusters (sometimes singly).

Little or no fragrance.

A plant which is vigorous, of rounded upright shape, and with semi-glossy, small foliage with pointed leaflets; the flowers and foliage being similar in size to the variety Scarlet Gem (miniature—U.S. Plant Pat. #2155). The plant which has a normal average height of 12" to 14" at maturity can be easily maintained at lesser height by occasional trimming.

A plant which grows and blooms satisfactorily both in greenhouse and outdoors; is a good plant for growing in pots; and provides excellent garden decoration as well as cut flowers.

The present variety of miniature rose was originated by me at my nursery located at Visalia, Calif., under conditions of careful control and observation, as a cross between Little Chief (a miniature rose, not patented) as the seed parent and Little Curt (miniature, not patented), as the pollen parent.

Subsequent to origination of the variety I successfully asexually reproduced it in my nursery located as aforesaid, by budding as well as by cuttings; the reproductions having run true in all respects.

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: hardy; dwarf; bush; seedling; greenhouse; outdoors; cut flowers; garden decoration; potted plant.

Class: Miniature.

Flowers:
- Continuity—continuous.
- Fragrance—little or none.

Flowers borne: Usually in clusters of 3 to 10 (or more) on normal strength medium length stems.

Quantity of bloom: Abundant both outside and in greenhouse.

Bud: Peduncle—medium length; slender; erect; medium green (sometimes tinted bronze, outdoors) very small short stiff hairs and sometimes some short prickles. Before calyx breaks, size—small. Form short; pointed with foliaceous appendages and numerous tiny short hairs on surface of the bud; with foliaceous parts extending beyond the tip of the bud equal to one-half or more of its length. Color—light to medium green, sometimes tinted bronze (outdoors). As calyx breaks, color—red. As first petal opens: red; size—small.
- Form: short; blunt or cup shaped; becoming rounded or high centered. Opening—opens well in all weather.

Bloom: Size when fully open—small, averaging 25—30 mm. (1–1¼").
- Petalage—very double—up to 60 petals (plus several narrow petaloids) arranged regularly.
- Form—slightly cupped at first, with petals rolled loosely outward, and later at maturity becoming high centered with petals being loosely rolled outward and with outer petals often rolled downward to give ball effect.

Petals: Fairly thick; satiny both inside and outside.
- Shape—outside petals nearly round (broad lanceolate with acute tip); intermediate—broad lanceolate with acute tip; inside narrow lanceolate.

Color: Newly opened flower from a plant grown outdoors (July 1975) Visalia, Calif.
- *Outside petal:* outside surface—near Chrysanthemum Crimson 824/3 shading to near white at base; inside surface—near Chrysanthemum Crimson 824 with both lighter and darker areas and shading to near white at base (in plastic house—Cardinal Red 822).
- *Intermediate petal:* outside surface—essentially same as outside petal; inside surface—essentially same as outside petal.
- *Inner petal:* outside surface—essentially same as intermediate petal; inside surface—similar to intermediate petal.
- General color effect newly opened flower—dark red. Three days open—usually red color is deeper.
- Behavior—spent petals usually hang on then entire old flower drops off, very lasting even in warm weather. Color is slightly lighter red (near Cardinal Red 822) in greenhouse and darker red (between Cardinal Red 822 and Chrysanthemum Crimson 824) outdoors.
- Flower longevity (June 1975)—bush in garden or pot—6–10 days. Cut flowers at living room temperature—4 to 7 days.

Reproductive organs:
- Stamens: Very few.
- Filaments: Short.
- Pollen: Little or none.
- Pistils: Dew.
- Styles: Fairly even; short; bunched.
- Ovaries: All enclosed in calyx.
- Hips: None.
- Sepals: Permanent; spear shaped; recurved; often 6 instead of the usual 5.
- Seed: None.

Foliage:
- Leaves—Compound of five leaflets (sometimes 7); abundant; small; leathery; semi-glossy to glossy.
- Leaflets—Shape: lanceolate; apex acute; base rounded or rounded acute. Margin serrate. Color: normal green; new growth often tinted bronze. Rachis: medium strength; upper side few short hairs or prickles, grooved, underside, several small hooked thorns. Stipules: medium length; narrow; medium length narrow points, turning out at an angle of 45 degrees or more.

Growth:
- Habit—dwarf; bushy; rounded; much branched.
- Growth—Free; vigorous.
- Canes—Medium; slender.
- Main stems—Color: dull green. Thorns: moderately thorny: medium length; hooked slightly downward; color—medium brown to gray. Prickles—usually none. Hairs—none.
- Branches—Color: medium green. Thorns: moderate-thorny; short; hooked slightly downward; medium length oval base. Prickles; none. Hairs: none.

New Shoots—Color: medium green, often tinted bronze. Thorns: moderately thorny; short; hooked slightly downward; sharp points; base narrow oval. Prickles: few to none.

The following is claimed:

1. A new and distinct variety of miniature rose plant of hardy, dwarf, rounded, much branched, bush type as illustrated and described, characterized by buds and flowers resembling the Scarlet Gem (Plant Pat. #2,155) miniature rose in general form and size but color is a rich deep red and flowers tending to be more rounded (ball shaped), the general color effect, both outdoors and in greenhouse; being deep red; and further characterized by a plant which is of vigorous and compact growth, easy to propagate from cuttings, with small semi-glossy foliage and an abundance of bloom, with flowers usually borne several to the stem in moderately tight clusters.

No references cited.

ROBERT E. BAGWILL, Primary Examiner